US008917816B2

(12) United States Patent
Ji et al.

(10) Patent No.: US 8,917,816 B2
(45) Date of Patent: Dec. 23, 2014

(54) MULTI-LEAF COLLIMATOR DEVICE FOR RADIOTHERAPY

(75) Inventors: Young Hoon Ji, Seoul (KR); Hai Jo Jung, Gyeonggi-Do (KR); Kum Bae Kim, Seoul (KR); Mun Sik Choi, Gyeonggi-Do (KR); Seung Woo Park, Seoul (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 344 days.

(21) Appl. No.: 13/582,297

(22) PCT Filed: Mar. 3, 2011

(86) PCT No.: PCT/KR2011/001450
§ 371 (c)(1),
(2), (4) Date: Aug. 31, 2012

(87) PCT Pub. No.: WO2011/108853
PCT Pub. Date: Sep. 9, 2011

(65) Prior Publication Data
US 2013/0000428 A1    Jan. 3, 2013

(30) Foreign Application Priority Data
Mar. 4, 2010  (KR) .................. 10-2010-0019571

(51) Int. Cl.
*A61N 5/10*  (2006.01)
*G21K 1/04*  (2006.01)

(52) U.S. Cl.
CPC .................... *A61N 5/1045* (2013.01)
USPC ....................... 378/152; 250/505.1

(58) Field of Classification Search
CPC .................. A61N 5/1045; G21K 1/046
USPC ........................ 378/152; 250/505.1
See application file for complete search history.

(56) References Cited

U.S. PATENT DOCUMENTS 6,792,078 B2 *   9/2004  Kato et al. ............. 378/152
2011/0026683 A1 *  2/2011  Broad et al. ............ 378/152

FOREIGN PATENT DOCUMENTS

| JP | 2002-136611 A | 5/2002 |
| JP | 2002-224230 A | 8/2002 |
| JP | 2009-160055 A | 7/2009 |
| JP | 2009-233279 A | 10/2009 |
| JP | 2009233279 A * | 10/2009 |
| KR | 100706758 B1 | 5/2007 |
| KR | 100740340 B1 | 7/2007 |

OTHER PUBLICATIONS

International Search Report: mailed Nov. 30, 2011; PCT/KR2011/001450.

* cited by examiner

*Primary Examiner* — Jack Berman
(74) *Attorney, Agent, or Firm* — Ladas & Parry LLP

(57) ABSTRACT

A multi-leaf collimator device for radiotherapy, including: a frame that has a box shape and has through-holes formed in top and bottom surfaces thereof; a plurality of collimators that are received in the frame, wherein each of the collimators includes a rack gear formed on the top surface of the collimator, the collimators are symmetrically arranged in a left-right direction about a central portion of the frame, and are slidably provided on the frame; and a motion driving unit that includes a pinion gear that is formed to be detachable from the rack gear formed on the top surface of the collimator, and is provided on the frame to move the pinion gear in a front-back direction of the frame and an up-down direction of the frame.

6 Claims, 6 Drawing Sheets

MULTI-LEAF COLLIMATOR DEVICE FOR RADIOTHERAPY

TECHNICAL FIELD

The present invention relates to a multi-leaf collimator device for radiotherapy, and more particularly, to a multi-leaf collimator device for radiotherapy, which may be provided in a radiotherapy device for treating a cancer patient or an animal and may precisely apply radiation to a treatment target portion.

The present invention is derived from a research project supported by the Atomic Energy Research & Development (R&D) Program of the Ministry of Education, Science, and Technology [Project No.: 20090062218, Project Name: Development of Internal Organ Motion Tracking Medical Physics Technology for Radiotherapy].

BACKGROUND ART

As nowadays many people have difficulties in maintaining good health due to stress and irregular meals in our complex society, it is very common for people to die from malignant tumors, i.e., cancer. Since the risk of cancer has constantly increased, effective counter measures are strongly needed. Therefore, recently, methods of treating cancer, and in particular, radiotherapy, have become important points of interest.

Two core elements are necessary for successful radiotherapy on tumors. First, radiation is required to be precisely applied to a tumor, and second, a planned radiation dose should be identical to a radiation dose which is actually applied.

A variety of displacement errors must be reduced in order to precisely apply radiation to a tumor. Displacement errors caused by a patient's body may be classified into three categories: a position related organ motion error, a gap fraction organ motion error, and an internal fraction organ motion error.

The position related organ motion error occurs due to changes in positions of a patient's internal organs according to a patient's posture, such as standing or lying down, while the patient is being treated. The position related organ motion error may be reduced by considering in advance the patient's posture for treating the patient and planning a treatment position.

The gap fraction organ motion error occurs due to changes in positions of a corresponding organ and its neighboring organs according to the filling degree of the bladder, rectum, or stomach. The gap fraction organ motion error may be removed by ensuring that the patient's condition during treatment planning and the actual treatment is the same.

The internal fraction organ motion error occurs due to changes in positions of a corresponding organ and its neighboring organs according to breathing or heartbeat. The internal fraction organ motion error is of physiological nature and occurs frequently in any living body. In particular, breathing has a significant effect and thus the internal fraction organ motion error is a serious problem affecting organs influenced by diaphragmatic respiration. Thus, the internal fraction organ motion error may be removed by tracing an external anatomic motion according to the patient's breath and applying radiation only to a specific part of an internal organ according to a change in a position of the specific part.

The inventors of the present invention have invented devices disclosed in Korean Patent Nos. 0706758 and 0740340.

However, if the above devices are used to apply radiation to a patient's portion to be treated, a radiation opening and closing device is opened only when an organ is at a specific position, which increases a time taken to actually treat the patient.

Meanwhile, in order to apply radiation to a patient's portion to be treated, a shield for protecting a normal tissue of the patient is manufactured and attached to a radiotherapy apparatus during an actual treatment. Examples of such shield include a generally used Lipowitz metal shield and a multi-leaf collimator (MLC). In the case of a Lipowitz metal shield, it takes one or two days to manufacture an alloy block, whereas in the case of an MLC, no shield is manufactured and the MLC may be more easily manufactured into various irradiation surfaces compared to the alloy block. However, conventional MLCs are expensive and do not operate in association with various radiation devices.

DETAILED DESCRIPTION OF THE INVENTION

Technical Problem

The present invention provides a multi-leaf collimator device for radiotherapy, which may continuously and precisely apply radiation only to a patient's portion to be treated and may be cheaper and more efficient than a conventional multi-leaf collimator device.

Technical Solution

According to an aspect of the present invention, there is provided a multi-leaf collimator device for radiotherapy, including: a frame that has a box shape and through-holes formed in top and bottom surface thereof; a plurality of collimators that are received in the frame, wherein each of the collimators includes a rack gear formed on the top surface of the collimator, and the collimators are symmetrically arranged in a left-right direction with respect to a central portion of the frame, and are slidably provided on the frame; and a motion driving unit that includes a pinion gear that is formed to be detachable from the rack gear formed on the top surface of the collimator, and is provided on the frame to move the pinion gear in a front-back direction of the frame and an up-down direction of the frame.

Advantageous Effects

A multi-leaf collimator device for radiotherapy according to the present invention effectively controls a multi-leaf collimator set to specify a radiation treatment area of a patient's portion. The present invention reduce the manufacturing costs and improve device efficiency, thereby leading to a more efficient treatment by effectively controlling the multi-leaf collimator. The multi-leaf collimator is controlled by a first motor and a second motor. The first motor controls a linear motion of the multi-leaf collimator. The second motor controls a rotational motion of a pinion gear.

BEST MODE

The present invention will now be described more fully with reference to the accompanying drawings, in which exemplary embodiments of the invention are shown.

Figure 1:
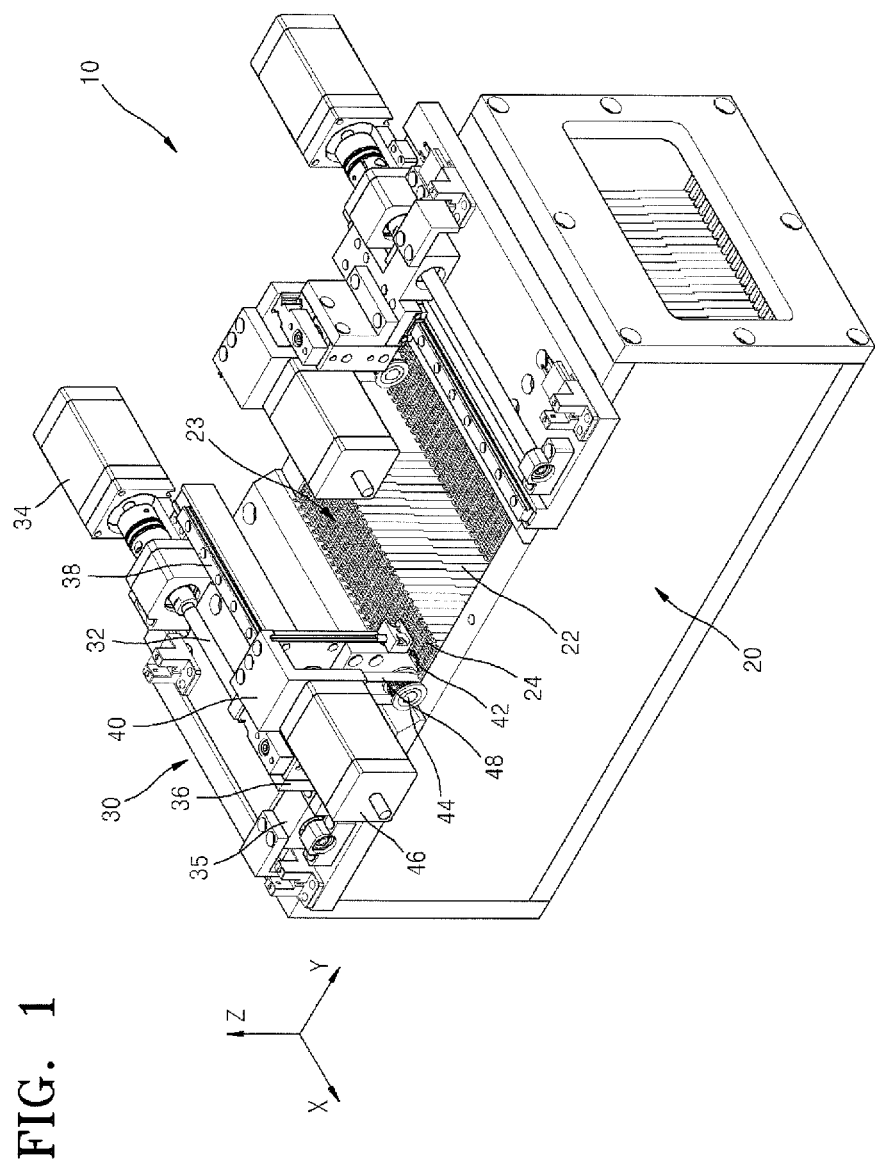
FIG. 1 is a perspective view illustrating a multi-leaf collimator device for radiotherapy according to an embodiment of the present invention.
Figure 2:
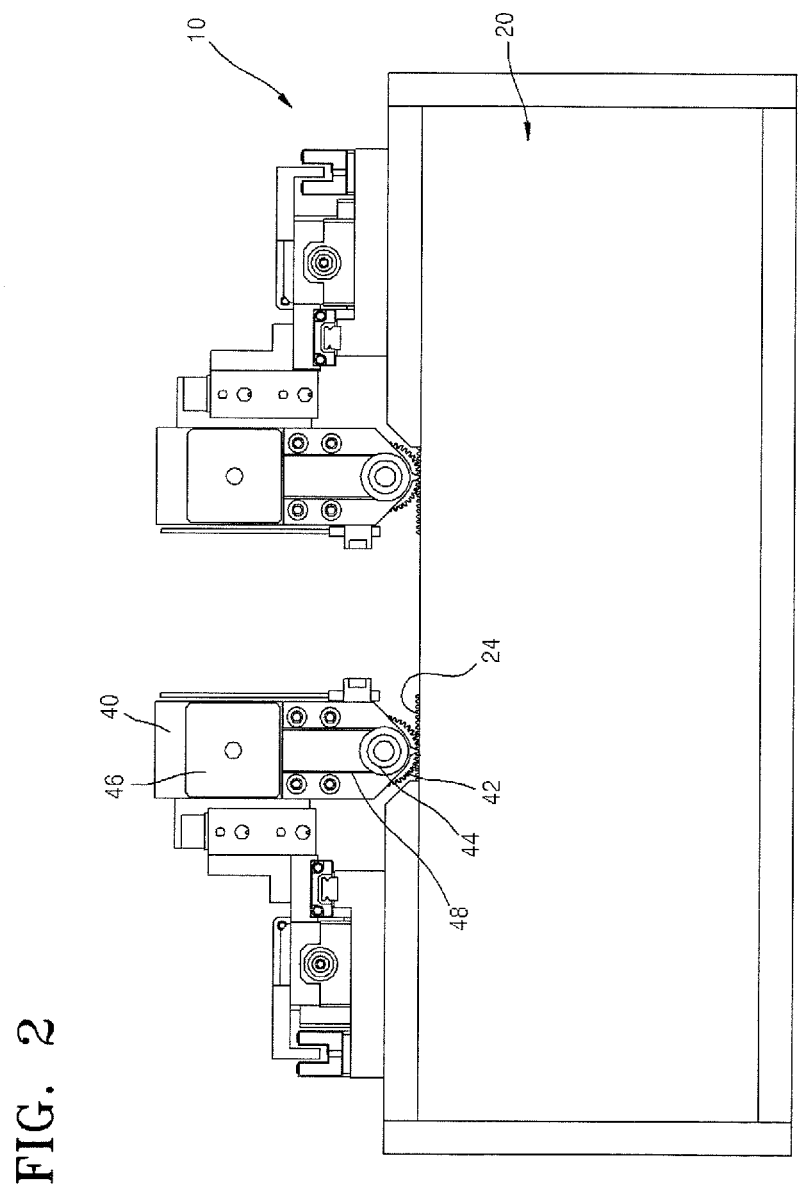
FIG. 2 is a front view illustrating the multi-leaf collimator device of FIG. 1.
Figure 3:
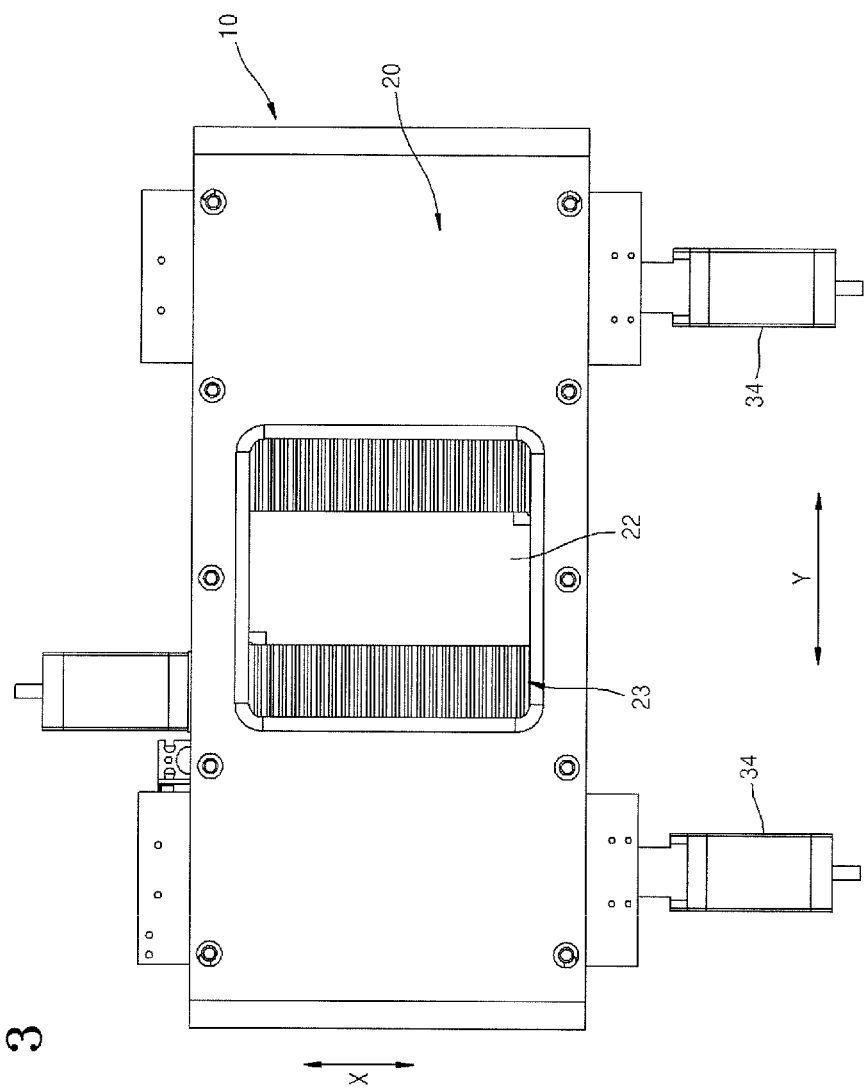
FIG. 3 is a bottom view illustrating the multi-leaf collimator device of FIG. 1.
Figure 4:
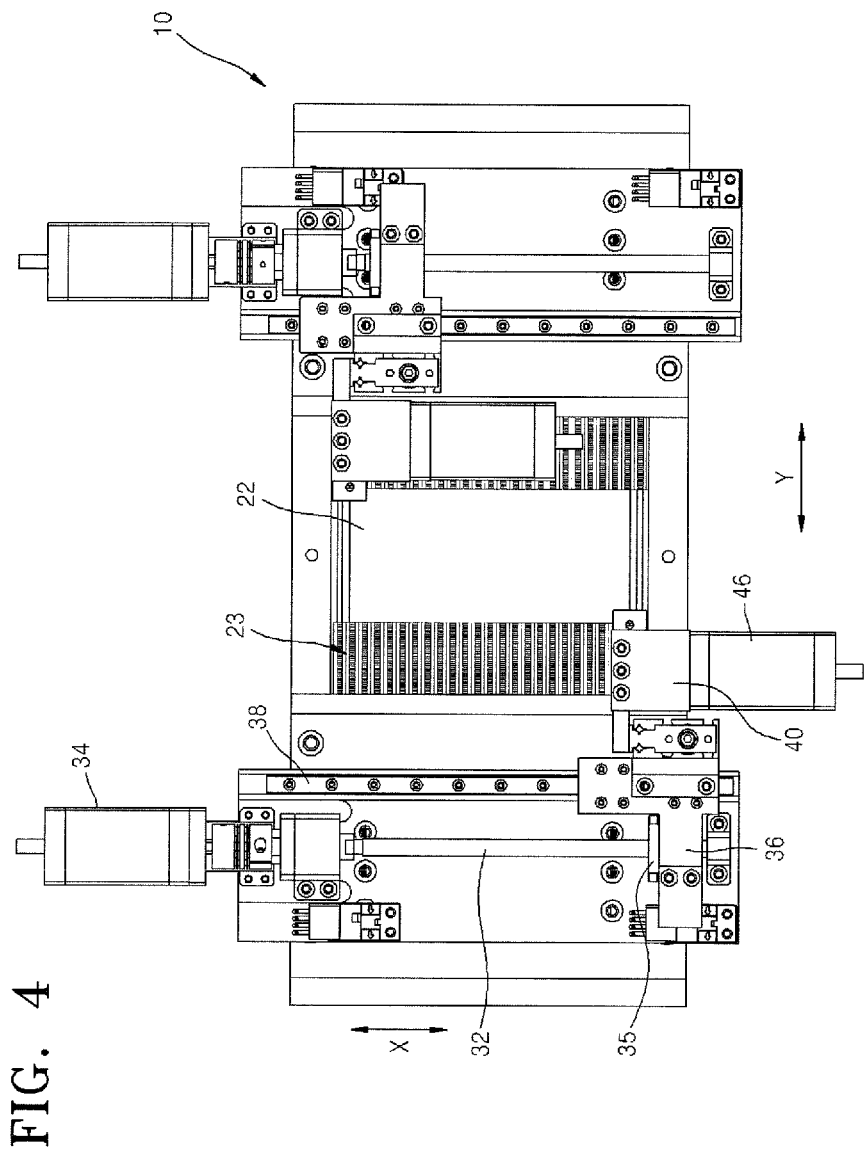
FIG. 4 is a plan view illustrating the multi-leaf collimator device of FIG. 1.
Figure 5:
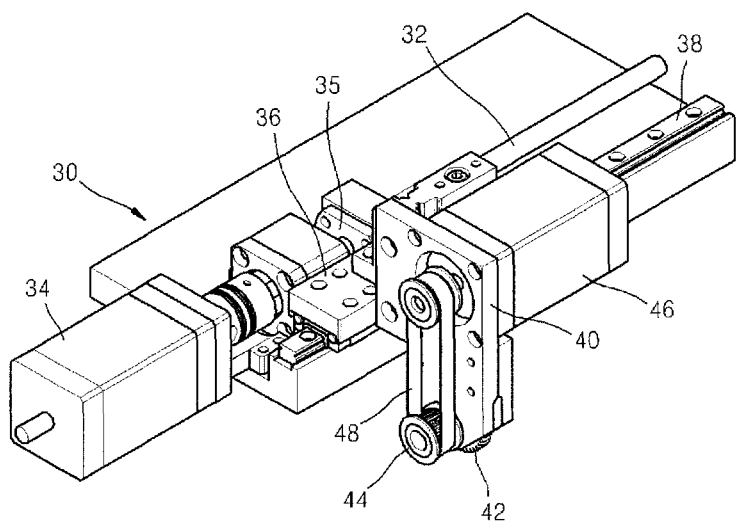
FIG. 5 is a view for explaining a motion driving unit of the multi-leaf collimator device of FIG. 1.
Figure 6:
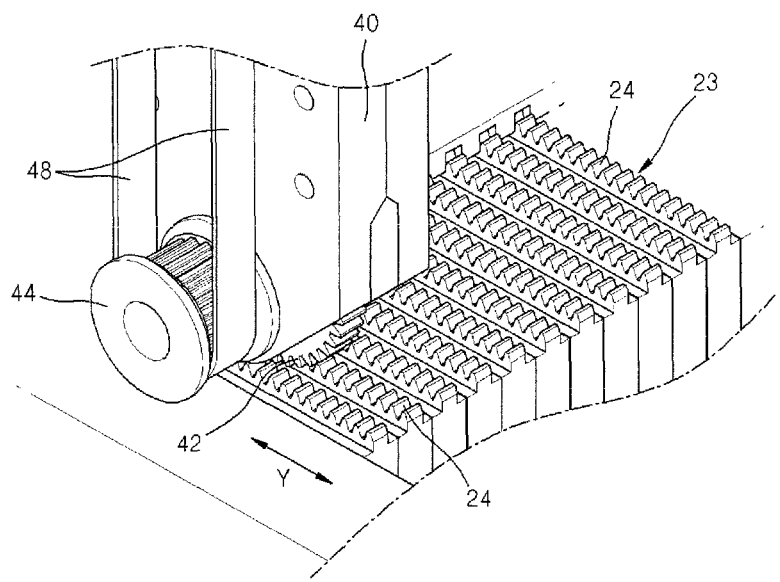
FIG. 6 is a view illustrating a case where a collimator is moved by the motion driving unit of FIG. 5.
Figure 7:
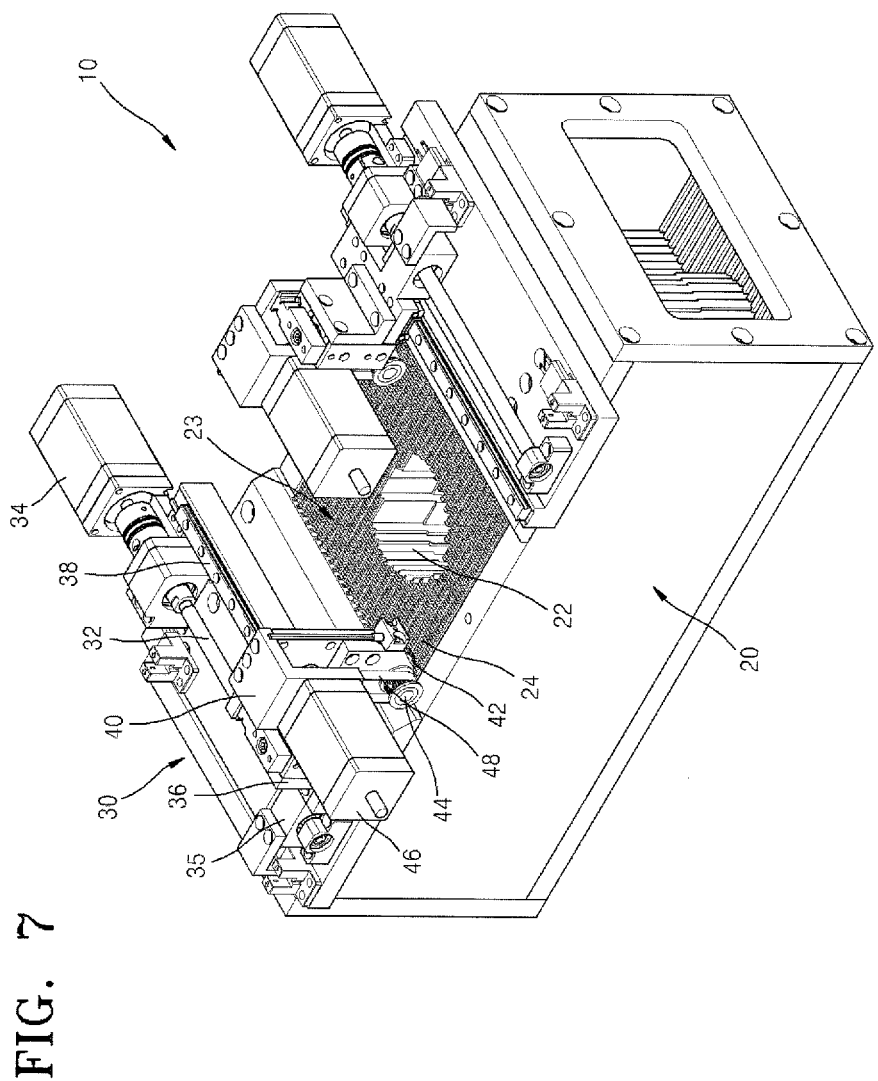
FIG. 7 is a view illustrating a case where the collimator is set to specify a radiation treatment area in the multi-leaf collimator device of FIG. 1.

FIG. 1 is a perspective view illustrating a multi-leaf collimator device 10 for radiotherapy, according to an embodiment of the present invention. FIG. 2 is a front view illustrating the multi-leaf collimator device 10 of FIG. 1. FIG. 3 is a bottom view illustrating the multi-leaf collimator device of FIG. 1. FIG. 4 is a plan view illustrating the multi-leaf collimator device 10 of FIG. 1. FIG. 5 is a view for explaining a motion driving unit 30 of the multi-leaf collimator device 10 of FIG. 1. FIG. 6 is a view illustrating a case where collimators 23 are moved by the motion driving unit 30 of FIG. 5. FIG. 7 is a view illustrating a case where the collimators 23 are set to define a radiation treatment area in the multi-leaf collimator device 10 of FIG. 1.

Referring to FIG. 1 through 7, the multi-leaf collimator device 10 is mounted on a radiotherapy apparatus for applying radiation to a patient's portion to be treated and is used to apply radiation only to the patient's portion to be treated.

The collimator device 10 includes a frame 20, the collimators 23, and the motion driving unit 30.

The frame 20 is fixed to the radiotherapy apparatus (not shown). The frame 20 is manufactured by combining a plurality of boards. The frame 20 is formed of a metal material such as carbon steel or an aluminum alloy. However, a material of the frame 20 is not limited to a metal material. The frame 20 has a box shape having an inner space. Through-holes 22 are formed in top and bottom surfaces of the frame 20. In the present embodiment, the through-holes 22 have rectangular shapes. Radiation applied by the radiotherapy apparatus passes through the through-holes 22.

The collimators 23 are received in the inner space of the frame 20 by being slidably provided in the frame 20. In detail, the collimators 23 are symmetrically arranged in a left-right direction Y with respect to a central portion of the frame 20. A rack gear 24 is formed on a top surface of each of the collimators 23. The collimators 23 are formed of a material capable of shielding radiation such as carbon steel or a tungsten alloy. Since the collimators 23 have a plate shape, the collimators 23 are referred to as a shield leaf.

The motion driving unit 30 moves the collimators 23 to form a desired shape and determines an area to which radiation is to be applied by the radiotherapy apparatus.

The motion driving unit 30 is provided on the frame 20. Two motion driving units 30 are symmetrically arranged in the left-right direction Y about the frame 20. Each of the motion driving units 30 includes a pinion gear 42 that is detachably coupled to the each of rack gears 24 formed on the collimators 23. The pinion gear 42 moves the collimators 23 in the left-right direction Y of the frame 20 and sets a radiation treatment area having a specific shape. The pinion gear 42 may be moved by the motion driving unit 30 in a front-back direction X of the frame 20 and an up-down direction Z of the frame 20.

The motion driving unit 30 includes a ball screw 32, a first motor 34, a ball nut 35, a moving member 36, a linear motion guide 38, an elevation member 40, the pinion gear 42, a pulley 44, a second motor 46, and a timing belt 48.

The ball screw 32 extends in a direction perpendicular to a direction in which the collimators 23 slide. In detail, as shown in FIG. 1, the ball screw 32 extends in the front-back direction X of the frame 20. An end portion of the ball screw 32 is coupled to an output shaft of the first motor 34. The other end portion of the ball screw 32 is rotatably provided on the frame 20. Accordingly, when the first motor 34 rotates, the ball screw 32 rotates. The first motor 34 is fixed to the frame 20. The first motor 34 may be a stepping motor or a servo motor having high precision.

The ball nut 35 is coupled to the ball screw 32. In general, the ball screw 32 and the ball nut 35 operate together to convert a rotational motion to a linear motion.

The moving member 36 is coupled to the ball nut 35. The moving member 36 is fixed to the ball nut 35 and integrally moves with the ball nut 35.

The linear motion guide 38 is disposed parallel to the ball screw 32. The moving member 36 is slidably coupled to the linear motion guide 38. The linear motion guide 38 enables the moving member 36 to linearly move more precisely.

The elevation member 40 is slidably coupled to the moving member 36. In detail, the elevation member 40 is elevatably coupled to the moving member 36. The elevation member 40 is elevatable by using air pressure. The elevation member 40 may be elevated by using air pressure by using well-known technology, and thus, a detailed explanation thereof will not be given.

The pinion gear 42 is provided on a lower end portion of the elevation member 40. The pinion gear 42 is rotatably provided on the elevation member 40. The pinion gear 42 protrudes from the lower end portion of the elevation member 40. The pulley 44 is coupled to a rotational shaft of the pinion gear 42. The pulley 44 is integrally coupled to the rotational shaft of the pinion gear 42 to smoothly connect to a driving source for rotating the pinion gear 42.

The second motor 46 is fixed to an upper end portion of the elevation member 40. A rotational shaft of the second motor 46 and the pulley 44 are connected to each other through the timing belt 48. Accordingly, when the rotational shaft of the second motor 46 rotates, the pulley 44 rotates through the timing belt 48 and the pinion gear 42 integrally coupled to the pulley 44 rotates too. The second motor 46 may be a stepping motor or a servo motor having high precision.

Motions of the first motor, the second motor 46, and the elevation member 40 may is be controlled by a computer (not shown). As such, the motion driving unit 30 may be controlled by the computer. Accordingly, the collimator device 10 may be efficiently controlled by inputting data necessary for a shape of a portion to be treated by using an input device such as a keyboard of the computer.

A case where a shape of a radiation treatment area as shown in FIG. 7 is set by using the multi-leaf collimator device 10 constructed as described above will be explained.

First, all of the collimators 23 of the multi-leaf collimator device 10 are gathered at the central portion of the frame 20. In an initial condition, since radiation is completely shielded by the collimators 23, no radiation is applied to the patient's portion to be treated.

A process of setting a shape of the radiation treatment area as shown in FIG. 7 to precisely apply radiation to the patient's portion to be treated will be explained. A user of the collimator device 10 inputs an arrangement shape of the collimators 23 to be set by using the input device of the computer. A condition input to the computer may be a graphic shape or a numerical condition. Once the condition is input, a central processing unit (CPU) of the computer generates control data for controlling the motion driving unit 30 of the collimator device 10. A driving signal of the motion driving unit 30 is transmitted from the computer. The motion driving unit 30 determines a position by driving the first motor 34 to move the moving member 36 in the front-back direction X. The motion driving unit 30 elevates the elevation member 40 in the up-down direction Z of the frame 20 by using air pressure and couples the pinion gear 42 to the rack gear 24. The motion driving unit 30 drives the second motor 46 to rotate the pulley 44. Once the pulley 44 rotates, the pinion gear 42 rotates and one of the collimators 23 moves in the left-right direction Y of the frame 20 due to the rack gear 24 coupled to the pinion gear 42. When a motion of one of the collimators 23 is completed, the elevation member 40 rises and the pinion gear 42 is separated from the rack gear 24. The first motor 34 is driven to move the pinion gear 42 to another one of the collimators 23. The shape of the radiation treatment area as shown in FIG. 7 may be set by repeatedly performing the process. The two motion driving units 30 may sequentially move the collimators 23 such that the collimators 23 form the required shape.

Since the collimators 23 received in the frame 20 are sequentially moved by the motion driving unit 30 by coupling the rack gear 24 and the pinion gear 42, the collimator device 10 may be effectively controlled. The collimator device 10 may reduce the risk of radiation exposure to users and may precisely arrange the collimators 23 compared to conventional collimator devices which manually control the collimator 23. Also, a conventional collimator device requires a driving unit for each of the collimators 23. However, since the collimator device 10 according to the present invention may be fabricated with reduced manufacturing costs compared to the conventional collimator device, the collimator device 10 may be used in applications where conventional collimator devices are not available because of high costs. In conclusion, the collimator device 10 may reduce the medical costs for patients.

While the present invention has been particularly shown and described with reference to exemplary embodiments thereof, it will be understood by those of ordinary skill in the art that various changes in form and details may be made therein without departing from the spirit and scope of the present invention as defined by the following claims.

MODE OF THE INVENTION

According to an aspect of the present invention, there is provided a multi-leaf collimator device for radiotherapy, including: a frame that has a box shape and through-holes formed in top and bottom surfaces thereof; a plurality of collimators that are received in the frame, wherein each of the collimators include a rack gear formed on a top surface of the collimator, the collimators are symmetrically arranged in a left-right direction about a central portion of the frame, and are slidably provided on the frame; and a motion driving unit that includes a pinion gear that is formed to be detachable from the rack gear formed on the top surface of the collimator, and is provided on the frame to move the pinion gear in a front-back direction of the frame and an up-down direction of the frame.

Two motion driving units may be symmetrically arranged in the left-right direction of the frame.

The motion driving unit may include: a ball screw that extends in a direction perpendicular to a direction in which the collimators slide; a first motor that is coupled to an end portion of the ball screw; a ball nut that is coupled to the ball screw; a moving member that is fixed to the ball nut; an elevation member that is elevatably coupled to the moving member; the pinion gear that is provided on a lower end portion of the elevation member to be rotatable relative to the elevation member; a pulley that is integrally coupled to a rotational shaft of the pinion gear; a second motor that is fixed to an upper end portion of the elevation member; and a timing belt that connects a rotational shaft of the second motor and the pulley.

The multi-leaf collimator device may further include a linear motion guide that is disposed parallel to the ball screw such that the moving member is slidable.

The elevation member may be elevatable by using air pressure.

The motion driving unit may be controlled by a computer.

The invention claimed is:

1. A multi-leaf collimator device for radiotherapy, comprising:
   a frame that has a box shape and through-holes formed in top and bottom surfaces thereof;
   a plurality of collimators that are received in the frame, wherein each of the collimators comprises a rack gear formed on a top surface of the collimator, and the collimators are symmetrically arranged in a left-right direction about a central portion of to the frame and are slidably provided on the frame; and
   a motion driving unit that comprises a pinion gear that is formed to be detachable from the rack gear formed on the top surface of the collimator, and is provided on the frame to move the pinion gear in a front-back direction of the frame and a up-down direction of the frame.

2. The multi-leaf collimator device of claim 1, wherein two motion driving units are symmetrically arranged in the left-right direction of the frame.

3. The multi-leaf collimator device of claim 1, wherein the motion driving unit comprises:
   a ball screw that extends in a direction perpendicular to a direction in which the collimator slides;
   a first motor that is coupled to an end portion of the ball screw;
   a ball nut that is coupled to the ball screw;
   a moving member that is fixed to the ball nut;
   an elevation member that is elevatably coupled to the moving member;
   the pinion gear that is provided on a lower end portion of the elevation member to be rotatable relative to the elevation member;
   a pulley that is integrally coupled to a rotational shaft of the pinion gear;
   a second motor that is fixed to an upper end portion of the elevation member; and
   a timing belt that connects a rotational shaft of the second motor and the pulley.

4. The multi-leaf collimator device of claim 3, further comprising a linear motion guide that is disposed parallel to the ball screw such that the moving member is slidable.

5. The multi-leaf collimator device of claim 3, wherein the elevation member is elevatable by using air pressure.

6. The multi-leaf collimator device of claim 5, wherein the motion driving unit is controlled by a computer.

* * * * *